US005130347A

United States Patent [19]
Mitra

[11] Patent Number: 5,130,347
[45] Date of Patent: Jul. 14, 1992

[54] PHOTOCURABLE IONOMER CEMENT SYSTEMS

[75] Inventor: Sumita B. Mitra, West St. Paul, Minn.

[73] Assignee: Minnesota Mining and Manufacturing Company, St. Paul, Minn.

[21] Appl. No.: 657,283

[22] Filed: Feb. 19, 1991

Related U.S. Application Data

[63] Continuation of Ser. No. 139,387, Dec. 30, 1987, abandoned.

[51] Int. Cl.$^5$ .......................... A61K 6/08; C08F 2/50; C08F 8/42; C08F 265/02
[52] U.S. Cl. .................................. 522/149; 433/228.1; 522/25; 522/81; 522/97; 522/129; 523/116; 523/117; 525/293; 525/342; 525/370
[58] Field of Search ...................... 525/293; 522/149

[56] References Cited

U.S. PATENT DOCUMENTS

| | | | |
|---|---|---|---|
| 2,549,732 | 4/1951 | Weaver | 528/274 |
| 2,568,331 | 9/1951 | Frilette | 525/19 |
| 2,628,209 | 2/1953 | Fisk | 523/514 |
| 2,673,151 | 2/1955 | Gerhart | 522/107 |
| 3,013,895 | 12/1961 | Agruss | 522/107 |
| 3,421,501 | 1/1969 | Beightol | 522/107 |
| 3,448,089 | 6/1969 | Celeste | 260/78.5 |
| 3,655,605 | 4/1972 | Smith | 260/29.6 M |
| 3,814,717 | 6/1974 | Wilson et al. | 260/29.6 M |
| 3,855,379 | 12/1974 | Araki | 525/293 |
| 3,872,047 | 3/1975 | Jandourek | 523/115 |
| 3,954,475 | 5/1976 | Bonham et al. | 96/67 |
| 4,016,124 | 4/1977 | Crisp et al. | 260/29.6 M |
| 4,035,321 | 7/1977 | Shahidi et al. | 260/22 CB |
| 4,089,830 | 5/1978 | Tezuka et al. | 260/29.6 H |
| 4,143,018 | 3/1979 | Crisp et al. | 260/29.6 M |
| 4,209,434 | 6/1980 | Wilson et al. | 260/29.6 H |
| 4,212,970 | 7/1980 | Iwasaki | 542/455 |
| 4,317,681 | 3/1982 | Beede et al. | 106/85 |
| 4,342,677 | 8/1982 | Muramatou et al. | 523/116 |
| 4,360,605 | 11/1982 | Schmitt et al. | 523/116 |
| 4,374,936 | 2/1983 | Tomioka et al. | 523/116 |
| 4,376,835 | 3/1983 | Schmitt et al. | 523/116 |
| 4,512,340 | 4/1985 | Buck | 522/96 |
| 4,719,149 | 1/1988 | Aasen | 522/83 |
| 4,732,943 | 3/1988 | Beech et al. | 522/123 |
| 4,746,686 | 5/1988 | Waller | 522/181 |
| 4,797,431 | 1/1989 | Billington | 523/116 |
| 4,813,876 | 3/1989 | Wang | 522/83 |
| 4,855,215 | 8/1989 | Nakano et al. | 430/283 |
| 4,872,936 | 10/1989 | Engelbrecht | 523/116 |

FOREIGN PATENT DOCUMENTS

WO88/05651 8/1988 World Int. Prop. O. .

OTHER PUBLICATIONS

Mathis et al., "Properties of a New Glass Ionomer/Composite Resin Hybrid Restorative" (Full paper, pp. 1–6 of Mathis et al., *J. Dent. Res.*, 66:113 (Abstract No. 51) (1987)).
R. L. Erickson et al., "Evaluation of Experimental Fluoride-Containing Restorative Materials" (Full paper, pp. 1–4 of R. L. Erickson et al., *J. Dent. Res.*, 66, Abstract No. 1114 (1987).
Prosser et al., "Polyelectrolyte Cements", Wilson and Prosser, eds., *Developments in Ionic Polymers*-1, Chapter 5, Applied Science Publishers (London and New York, 1983).
Prosser et al., *J. Chem. Tech. Biotechnol.*, 29, 69–87 (1979).
"Radiation Curing", Kirk-Othmer Encyclopedia of Chemical Technology, 3d Ed., vol. 19, pp. 607–624 (1982).
Heilman et al., "Chemistry of Alkenyl Azalactones I. Radiation Sensitive Materials Derived from Azlactone Containing Copolymers", *J. Polym. Sci., Polym. Chem. Ed.* 22, 1179–1186 (1984).
Swartz et al., *J. Dent. Res.*, 63, 158–160 (1984).

*Primary Examiner*—Marion E. McCamish
*Assistant Examiner*—Arthur H. Koeckert
*Attorney, Agent, or Firm*—Gary L. Griswold; Walter N. Kirn; Dale A. Bjorkman

[57] ABSTRACT

A dental cement system containing a photocurable ionomer, reactive powder and water undergoes both a conventional setting reaction and a photocuring reaction.

The cement system can provide a long working time and can be cured on demand by exposure to an appropriate source of radiant energy. The surface of the cement cured in this manner is then hard enough to allow subsequent clinical procedures to be performed, while the ongoing chemical-cure "setting" reaction hardens the remainder of the cement.

13 Claims, No Drawings

PHOTOCURABLE IONOMER CEMENT SYSTEMS

This is a continuation of application Ser. No. 07/139,387 filed Dec. 30, 1987, now abandoned.

TECHNICAL FIELD

The present invention relates to ionomer cement systems useful, for instance, for the preparation of dental and medical adhesives, bases, liners, luting agents, sealants, and filling materials for restorative and/or endodontic use. This invention also relates to methods and compositions for setting and curing such cement systems. In another aspect this invention relates to the ionomers useful in such systems, as well as to methods of using such ionomers, and the cements formed with such ionomers.

BACKGROUND ART

The setting reaction of ionomer cements is known mainly through studies of glass ionomer cements, i.e., ionomer cements in which the powder used in the cement is an ion-leachable glass, such as those based on calcium aluminosilicate glasses, or more recently, borate glasses. See generally, Prosser et al., "Polyelectrolyte Cements", Wilson and Prosser, eds., *Developments in Ionic Polymers*-1, Chapter 5, Applied Science Publishers (London and New York, 1983). In the setting reaction, the powder behaves like a base and reacts with the acidic polyelectrolyte, i.e., ionomer, to form a metal polysalt which acts as the binding matrix. Water serves as a reaction medium and allows the transport of ions in what is essentially an ionic reaction.

The setting reaction is therefore characterized as a chemical cure system that proceeds automatically upon mixing the ionomer and powder in the presence of water. The cements set to a gel-like state within a few minutes and rapidly harden to develop strength. See, e.g., Prosser et al., *J. Chem. Tech. Biotechnol.*, 29, 69–87 (1979). Chelating agents, such as tartaric acid, have been described as useful for modifying the rate of setting, e.g., to provide longer working times for the cements. See, e.g., U.S. Pat. Nos. 4,089,830, 4,209,434, 4,317,681 and 4,374,936. Unfortunately, when working times are lengthened by the usual methods, setting times are generally also lengthened.

Many commercially available glass ionomer cements include such chelating agents, and as a result are characterized by working times that are on the order of 1 to 2 minutes, but relatively long setting times, e.g., on the order of 4 to 15 minutes. During this set time a dry field must be maintained, and yet dessication of the cement must be avoided. Such conditions can lead to discomfort for the patient as well as the added burden of having to spend extra time in the dentist's chair. Thus present day glass ionomer cements, although beneficial clinically, are quite technique-sensitive, as well as time-consuming for the dentist and patient.

Of peripheral relevance to the present invention, but worth noting nonetheless, Mathis et al., *J. Dent. Res.*, 66:113 (Abst. No. 51) (1987), reports the addition of a separate light curable composite resin to the liquid component of an ionomer in order to form a "hybrid" material. This hybrid material was cured by exposure to a visible light source immediately after mixing it with powder.

SUMMARY OF THE INVENTION

Further adjustability of working time and setting time would be desirable in order to provide greater flexibility in the formulation of ionomer cement systems, and in particular, glass ionomer cement systems. Such adjustability is also desirable in order to extend the practical application of such cement systems to uses involving higher glass loading levels (e.g., for posterior or incisal applications) or lower mix viscosity (e.g., endodontic sealants) than are attainable using current techniques.

The present invention provides, in one aspect, ionomer cement systems that are photocurable using radiant energy. Such systems provide the opportunity to achieve long working times as well as short setting times. These systems are prepared using photocurable ionomers which comprise a polymer having sufficient pendent ionic groups to undergo a setting reaction in the presence of a reactive powder and water, and sufficient pendent polymerizable groups to enable the resulting mixture to be cured by exposure to radiant energy.

The invention also provides methods for preparing and methods for using such photocurable ionomer cement systems. In another aspect the present invention also provides novel photocurable ionomers.

The photocurable ionomer cement system of the present invention comprises (a) photocurable ionomer as described herein, and (b) reactive powder. Preferred optional ingredients of the photocurable ionomer system include water (present in a form that does not prematurely begin to set the system), appropriate polymerization initiators, modifying agents, and copolymerizable and non-copolymerizable cosolvents. Other optional ingredients include pigments, fillers (e.g., pulverized precious or nonprecious metals, silica, quartz or metal oxides), and the like.

The photocurable ionomer cement systems of the present invention can be used to prepare a cement by combining the ionomer and the reactive powder in the presence of water. As with present day cement systems, the water serves as a reaction medium allowing the transport of ions between the ionomer and the reactive powder, thereby allowing the acid-base chemical cure "setting" reaction to occur. This setting reaction can also be termed the "dark reaction" in that it will proceed regardless of the presence of light or any other form of radiant energy.

The systems of the present invention provide a valuable and time-saving opportunity to cure the system rapidly and on demand by a brief exposure to an appropriate source of radiant energy after the necessary components have been mixed and the setting reaction has begun, but while the cement is still in a fluid or plastic, i.e., "workable", state. As a result, the practitioner can achieve long working times by the use of modifying agents to slow the setting reaction, but need not be burdened with the typical correspondingly long setting times. By the use of modifying agents as discussed in greater detail below, the resultant systems can be made to have sufficiently long working times for use in new medical and dental applications where ionomer cements have not hitherto been employed.

Applicant has also discovered that certain modifying agents traditionally used in glass ionomer cement systems, e.g., tartaric acid, do not provide longer working times when used in the systems of the present invention. Applicant has discovered that a new group of compounds can be used as modifying agents in order to provide the desired result of prolonged working times.

Moreover, by the use of fluoride-containing reactive powders, as explained more fully below, the present invention provides the ability to prepare a dental restorative that is both photocurable and capable of exhibiting cariostatic fluoride release. Such a combination of properties is highly desirable.

DETAILED DESCRIPTION

The term "photocurable ionomer", as used herein, refers to a polymer having sufficient pendent ionic groups to undergo a setting reaction in the presence of a reactive powder and water, and sufficient pendent polymerizable groups to enable the resulting mixture to be polymerized, i.e., cured, upon exposure to radiant energy.

The term "reactive powder", as used herein, refers to a metal oxide or hydroxide, mineral silicate, or ion-leachable glass that is capable of reacting with the ionomer in the presence of water to form a hydrogel.

The term "ionomer cement system", as used herein, refers to the unmixed, or mixed but unset and uncured, combination of photocurable ionomer, reactive powder, and other optional ingredients, such as water. Such systems include kits in which the ionomer is employed as a concentrated aqueous solution, for mixing directly with the powder, as well as kits in which the ionomer is employed in a dry blend with the powder, for later mixing with water.

The term "working time", as used herein, refers to the time between the beginning of the setting reaction, i.e., when the ionomer and reactive powder are combined in the presence of water, and the time the setting reaction has proceeded to the point at which it is no longer practical to perform further physical work upon the system, e.g., spatulate it or reform it, for its intended dental or medical purpose.

The term "setting time", as used herein, refers to the time between the beginning of the setting reaction in a restoration, and the time sufficient hardening has occurred to allow subsequent clinical procedures to be performed on the surface of the restoration. Such hardening can occur either in the course of the normal setting reaction and/or by curing a photocurable system.

Photocurable ionomers of the present invention comprise a polymer having sufficient pendent ionic groups to undergo a setting reaction in the presence of a reactive powder and water, and sufficient pendent polymerizable groups to enable the resulting mixture to be cured by exposure to radiant energy.

Preferred photocurable ionomers have the general Formula I:

$$B(X)_m (Y)_n \qquad \text{I}$$

wherein
B represents an organic backbone,
each X independently is an ionic group capable of undergoing a setting reaction in the presence of water and a reactive powder,
each Y independently is a photocurable group,
m is a number having an average value of 2 or more, and
n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with either the photocuring reaction of the photocurable ionomer or its dark reaction with the reactive powder.

Preferred X groups are acidic groups, with carboxyl groups being particularly preferred.

Suitable Y groups include, but are not limited to, polymerizable ethylenically unsaturated groups and polymerizable epoxy groups. Ethylenically unsaturated groups are preferred, especially those that can be polymerized by means of a free radical mechanism, examples of which are substituted and unsubstituted acrylates, methacrylates, alkenes and acrylamides. In aqueous systems, polymerizable groups that are polymerized by a cationic mechanism, e.g., polymerizable ethylenically unsaturated groups such as vinyl ether groups and polymerizable epoxy groups, are less preferred since a free radical mechanism is typically easier to employ in such systems than a cationic mechanism.

X and Y groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups.

Photocurable ionomers of Formula I can be prepared according to a variety of synthetic routes, including, but not limited to, (1) reacting n X groups of a polymer of the formula $B(X)_{m+n}$ with a suitable compound in order to form n pendent Y groups, (2) reacting a polymer of the formula $B(X)_m$ at positions other than the X groups with a suitable compound in order to form n pendent Y groups, (3) reacting a polymer of the formula $B(Y)_{m+n}$ or $B(Y)_n$, either through Y groups or at other positions, with a suitable compound in order to form m pendent X groups, and (4) copolymerizing appropriate monomers, e.g., a monomer containing one or more pendent X groups and a monomer containing one or more pendent Y groups.

The first synthetic route referred to above is preferred, i.e., the reaction of n X groups of a polymer of the formula $B(X)_{m+n}$ to form n pendent Y groups. Such groups can be reacted by the use of a "coupling compound", i.e., a compound containing both a Y group and a reactive group capable of reacting with the polymer through an X group in order to form a covalent bond between the coupling compound and the X group, thereby linking the Y group to the backbone B in a pendent fashion. Suitable coupling compounds are organic compounds, optionally containing non-interfering substituents and/or non-interfering linking groups between the Y group and the reactive group.

Particularly preferred photocurable ionomers of Formula I are those in which each X is a carboxyl group and each Y is an ethylenically unsaturated group that can be polymerized by a free radical mechanism. Such ionomers are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group. The molecular weight of the resultant photocurable ionomers is preferably between about 250 and about 500,000, and more preferably between about 5,000 and about 100,000. These ionomers are generally water-soluble, but to a lesser extent than the polyalkenoic acids from which they are derived. Hence, the use of cosolvents, as described more fully below, is preferred in order to enhance the solubility of the ionomers and achieve more concentrated solutions thereof.

Suitable polyalkenoic acids for use in preparing ionomers of this invention include those homopolymers and copolymers of unsaturated mono-, di-, or tricarboxylic acids commonly used to prepare glass ionomer cements. Representative polyalkenoic acids are described, for example, in U.S. Pat. Nos. 3,655,605, 4,016,124, 4,089,830, 4,143,018, 4,342,677, 4,360,605 and 4,376,835.

Preferred polyalkenoic acids are those prepared by the homopolymerization and copolymerization of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid and tiglic acid. Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyethyl methacrylate. Ter- and higher polymers may be used if desired. Particularly preferred are the homopolymers and copolymers of acrylic acid. The polyalkenoic acid should be surgically acceptable, that is, it should be substantially free from unpolymerized monomers and other undesirable components.

Particularly preferred polyalkenoic acids also include homopolymers of polyacrylic acid, and copolymers of acrylic and itaconic acids, acrylic and maleic acids, methyl vinyl ether and maleic anhydride or maleic acid, ethylene and maleic anhydride or maleic acid, and styrene and maleic anhydride or maleic acid.

Polymers of formula $B(X)_{m+n}$ can be prepared by copolymerizing an appropriate mixture of monomers and/or comonomers. Preferably, such polymers are prepared by free radical polymerization, e.g., in solution, in an emulsion, or interfacially. Such polymers can be reacted with coupling compounds in the presence of appropriate catalysts, as described more fully in the examples below.

Coupling compounds suitable for use for preparing the preferred ionomers of the present invention include compounds that contain at least one group capable of reacting with X in order to form a covalent bond, as well as at least one polymerizable ethylenically unsaturated group. When X is carboxyl, a number of groups are capable of reacting with X, including both electrophilic and nucleophilic groups. Examples of such groups include the following moieties, and groups containing these moieties: —OH, —NH$_2$, —NCO, —COCl, and

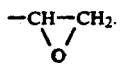

Examples of suitable coupling compounds include, but are not limited to, acryloyl chloride, methacryloyl chloride, vinyl azalactone, allyl isocyanate, 2-hydroxyethylmethacrylate, 2-aminoethylmethacrylate, and 2-isocyanatoethyl methacrylate. Other examples of suitable coupling compounds include those described in U.S. Pat. No. 4,035,321, the disclosure of which is hereby incorporated by reference. Examples of preferred coupling compounds include, but are limited to, the following methacrylate compounds and their corresponding acrylates.

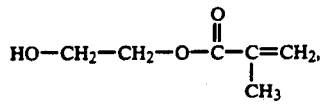

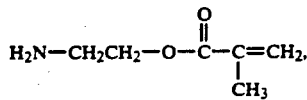

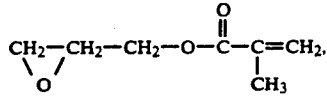

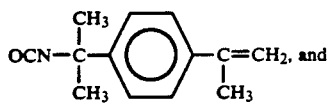

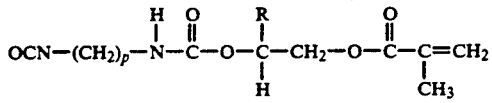

wherein p is 1 to 20 and R is H or lower alkyl (e.g., having 1 to 6 carbon atoms), as well as the following allyl compound

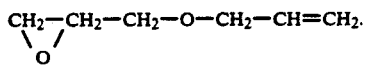

Particularly preferred coupling compounds are the following methacrylate compounds and their corresponding acrylates, wherein R is as defined above.

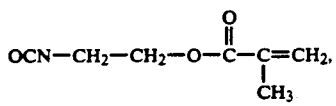

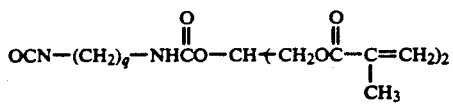

wherein q is 1 to 18.

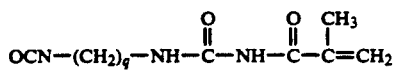

wherein q is as defined above,

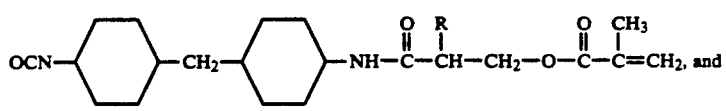

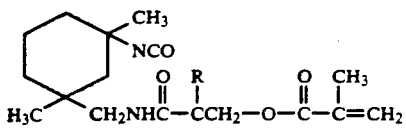

Preferred photocurable ionomers of Formula I are by reacting a polymer of formula $B(X)_{m+n}$ wherein X is COOH with a coupling compound containing a reactive group of the formula NCO. The resultant ionomers, e.g., those of Formula I above wherein the covalent bond between the X group and the reactive group of the coupling compound is an amide linkage, are believed novel and provide an optimal combination of such properties as adhesion to dentin, mechanical strength, working time, fluoride release and the like.

The preferred photocurable ionomers of the present invention can be formulated in water, either alone or with the use of adjuvants such as cosolvents described in greater detail below. The preferred concentration of ionomer in aqueous solution is between about 10 and about 70 percent by weight, based on the weight of the final aqueous solution, and more preferably is between about 20 and about 50 percent by weight. For optimal use in preparing a cement of the present invention, the preferred viscosity of the ionomer solution is between about 60 and about 900 centistokes, and most preferably between about 150 and about 500 centistokes. Ionomer solutions having higher viscosities will generally be more difficult to mix, and solutions of lower molecular weight ionomer will generally provide cements having lower strength.

In order to prepare a photocurable ionomer cement from the cement system of this invention, a photocurable ionomer is mixed with a reactive powder in the presence of water. Optionally, and preferably, the cement system also includes modifying agent and polymerization initiator, thereby providing the ability to achieve a longer working time and a shorter setting time, respectively, when preparing the resultant cement.

Reactive powders suitable for use in the cement systems of this invention include those that are commonly used with ionomers to form ionomer cements. Examples of suitable reactive powders are described in the Prosser et al. article cited above, the disclosure of which is hereby incorporated by reference, as well as metal oxides such as zinc oxide and magnesium oxide, and ion-leachable glasses, e.g., as described in U.S. Pat. Nos. 3,655,605, 3,814,717, 4,143,018, 4,209,434, 4,360,605 and 4,376,835.

Particularly preferred reactive powders for use in the cement systems of this invention are those that contain leachable fluoride, since the sustained release of fluoride ions as a byproduct of the setting reactions provides cariostatic benefits. Examples of preferred powders include fluoroaluminosilicate and fluoroaluminoborate ion-leachable glasses.

The ionomer cement systems of the invention can frequently be polymerized without the use of one or more polymerization initiators, e.g., by the use of thermal energy or by exposure to a high energy pulsed xenon source. Optionally, and preferably, the ionomer cement system contains one or more suitable polymerization initiators that act as a source of free radicals when activated. Such initiators can be used alone or in combination with one or more accelerators and/or sensitizers.

Polymerization initiators suitable for use in the present invention include electromagnetic radiation-induced polymerization initiators, such as ultraviolet- or visible-light-induced polymerization initiators, that exhibit a desired combination of such properties as stability and efficiency of free radical production and polymerization initiation.

Examples of suitable ultraviolet-induced polymerization initiators include, but are not limited to, ketones such as benzil and benzoin, and acyloins and acyloin ethers, commercially available, for example, from Aldrich Chemical Co. Preferred ultraviolet-induced polymerization initiators include 2,2-dimethoxy-2-phenylacetophenone ("Irgacure 651") and benzoin methyl ether (2-methoxy-2-phenylacetophenone), both commercially available from Ciba-Geigy Corp.

Examples of suitable visible-light-induced initiators include, but are not limited to, diaryliodonium salts and triarylsulfonium salts, as well as chromophore substituted halomethyl-s-triazines, such as those described in U.S. Pat. No. 3,954,475, and halomethyl oxadiazoles such as those described in U.S. Pat. No. 4,212,970. Such initiators can be used alone or in combination with suitable accelerators, e.g., amines, peroxides, and phosphorus compounds, and/or with suitable photosensitizers, e.g., ketone or alpha-diketone compounds.

For photocurable ionomers that are polymerized by a cationic mechanism, suitable initiators include salts that are capable of generating cations such as the diaryliodonium, triarylsulfonium and aryldiazonium salts.

Preferred visible light-induced polymerization initiator systems include suitable combinations of a diketone, e.g., camphorquinone, and a diaryliodonium salt, e.g., diphenyliodonium chloride, bromide, iodide or hexafluorophosphate, with or without additional hydrogen donors, or accelerators, such as sodium benzene sulfinate, amines or amine alcohols.

Polymerization initiator, when employed, is preferably present in the ionomer cement system in an amount sufficient to achieve the desired extent of polymerization. Such amount is dependent in part on the extinction coefficient of the initiator and the thickness of the layer to be exposed to radiant energy. Typically, an ultraviolet-induced polymerization initiator will be present at about 0.01% to about 5%, based on the weight of the ionomer(s) present, and the components of a visible light-induced polymerization initiator system will generally be present at a combined weight of about 0.01 to 5%, and preferably from about 0.1 to 5%, based on the weight of the ionomer(s) present.

The components of the photocurable ionomer cement system can be combined, e.g., blended or mixed, in a variety of manners and amounts in order to form the photocurable ionomer cement of this invention. Suitable combining techniques include those commonly employed to mix ionomer cement systems.

In one suitable technique, a concentrated aqueous solution of photocurable ionomer is mixed with reactive powder at the time of use. The resultant combination of ionomer, powder and water allows the setting reaction to begin.

In an alternative technique, the photocurable ionomer and powder are provided as a powdered blend under substantially anhydrous conditions, i.e., conditions in which there is not sufficient water to allow the setting reaction to proceed. Such systems can then be combined with water at the time of use in order to begin the setting reaction.

The ratio of powder (i.e., reactive powder or powdered blend of ionomer and reactive powder) to liquid in such techniques is an important factor in determining the workability of the mixed ionomer cement systems. Ratios higher than about twenty to one (powder to liquid, by weight) tend to exhibit poor workability, while ratios below about one to one tend to exhibit poor mechanical properties, e.g., strength, and hence are not preferred. Preferred ratios are on the order of about one to one to about five to one.

Optional other ingredients, such as polymerization initiators, modifying agents and cosolvents can be added at any time and in any manner that does not prematurely begin the setting reaction or the photocuring reaction. Modifying agents can be used in the ionomer cement systems of the present invention in order to provide prolonged working times. Applicant has discovered a new group of compounds useful as modifying agents in the systems of the present invention.

Modifying agents useful in the cement system of the present invention are selected from the group consisting of alkanolamines, e.g., ethanolamine and triethanolamine, and mono-, di- and tri-sodium hydrogenphosphates.

Modifying agents can either be incorporated into an aqueous solution of the ionomer, or can be milled with the powder to be used in the ionomer cement system. The modifying agents are preferably used at a concentration between about 0.1 to about 10 percent by weight, based on the weight of the reactive powder, and preferably between about 0.5 to about 5 percent.

Cosolvents useful in the present invention include, but are not limited to, low molecular weight organic solvents. The word "cosolvent", as used herein refers to a material that aids in the dissolution of a photocurable ionomer in water, in order to form a homogeneous aqueous solution of cosolvent and ionomer. Suitable cosolvents include non-copolymerizable organic solvents and copolymerizable low molecular weight hydrophilic alkenyl solvents. The word "copolymerizable" as used herein refers to the ability of the cosolvent to cure compatibly with the ionomers used in the invention. Copolymerizable cosolvents can be added to the ionomer cement systems of this invention for a variety of reasons, for instance, to provide a homogeneous solution of a photocurable ionomer having inherently low aqueous solubility, to shorten the exposure of radiant energy needed to cure the system, or to vary the physical properties, e.g., the flexibility, of the resultant cured ionomer cement. Examples of suitable cosolvents include non-copolymerizable cosolvents such as ethanol, propanol, and glycerol, and copolymerizable cosolvents such as 2-hydroxylethylmethacrylate or 2-hydroxypropylmethacrylate.

Sufficient amounts of each component in the cement systems of the present invention should be employed to obtain the desired working time. Preferably such systems will provide a working time of at least about one minute and most preferably greater than two minutes, during which time the systems can be cured by exposure to an appropriate source of radiant energy. For the sake of brevity this discussion will focus on dental applications, and particularly, the curing of such systems in situ, e.g., in the mouth of a patient.

The curing of the ionomer cement system is accomplished by exposure to any source of radiant energy capable of causing the desired extent of polymerization of the photocurable ionomer. Suitable radiant energy sources afford a desired combination of such properties as safety, controllability, suitable intensity, and suitable distribution of incident energy. See generally, "Radiation Curing", Kirk-Othmer Encyclopedia of Chemical Technology, 3d Ed., Vol. 19, pp. 607–624 (1982). Preferred radiant energy sources are ultraviolet or visible light sources whose emission spectra correspond closely with the absorption range of the polymerization initiator in the ionomer cement system. For instance, sources emitting ultraviolet light at wavelengths between about 335 and 385 nm, and sources emitting visible light in the blue region at wavelengths between about 420 and 480 nm are preferred for use with the preferred ultraviolet- and visible-light-induced polymerization initiators, respectively. For polymerizing cement systems in the mouth, visible light radiation such as that provided by standard dental curing lights is particularly preferred.

Upon exposure of an ionomer cement system of the present invention to an appropriate source of radiant energy, the system rapidly begins to cure, e.g., within about 45 seconds, and preferably within about 30 seconds. The restoration generally exhibits the greatest degree of cure at its surface, where the radiant energy is most intense. The surface of the restoration therefore can be cured sufficiently to allow subsequent procedures to be performed on the restoration, while the interior of the restoration is allowed to harden fully by means of the ongoing setting reaction. Thus, if the curing step is omitted, the usual setting reaction will occur, ultimately resulting in the hardening of the material, even in the dark. This phenomenon offers a unique advantage in that a relatively deep restoration can be prepared by rapidly curing the outer surface of the restoration instantly by exposure to radiant energy, allowing the inner portions of the restoration to cure more slowly by the usual setting reaction. As a result, the dentist can continue to carry out further restorative procedures, e.g., layering further ionomer cement on the hardened surface, while the inner portions continue to harden. This can result in a substantial saving of time for the practitioner and patient.

The ionomer cements of this invention can be used in a variety of applications in the dental or medical fields in which a bulk curable material of low shrinkage is desired that will adhere well to the surrounding tooth or bone structure. For instance, these cements can be used as dental restoratives for lining or basing Class I, II, III and V restorations, for cementation, as sealants, and as bulk filling materials.

The present invention will be further understood in view of the following examples which are merely illustrative and not meant to limit the scope of the invention. Unless otherwise indicated, all parts and percentages are by weight.

EXAMPLE 1

Synthesis of Low Molecular Weight Polyacrylic Acid

A glass reactor fitted with two addition funnels, a thermometer, a mechanical stirrer, a reflux condenser and a nitrogen inlet tube was charged with 354.4 parts dry tetrahydrofurna ("THF") (water content <0.02%). A solution of 144 parts acrylic acid monomer in 82.4 parts THF was charged into one of the addition funnels. A solution of 1.64 parts azobisisobutyronitrile ("AIBN") initiator in 102 parts THF was charged into the second funnel. The nitrogen purge was started and the reactor heated. When a temperature of approximately 60° C. was attained in the reactor vessel, the monomer solution was added at a rate of about 9 parts every 5 minutes and initiator solution was added at a rate of about 4.5 parts every 5 minutes After the additions were complete, the reaction was allowed to proceed at about 60° C. for an additional 2 hours, resulting in a homogeneous, slightly hazy solution Gel permeation chromatography ("GPC") showed the weight average molecular weight ($M_w$) of the resultant polymer to be 9,700 with a polydispersity of 2.7.

EXAMPLE 2

Synthesis of High Molecular Weight Polyacrylic Acid

Nitrogen gas was bubbled into a solution of 15 parts acrylic acid, 82.5 parts p-dioxane and 0.15 parts of AIBN for a period of 15 minutes. The reaction vessel was then stoppered and heated at about 60° C. for approximately 18 hours, at which time infrared spectral analysis showed the absence of C=C bands at 1635 cm$^{-1}$. Gel permeation chromatography of the homogeneous, clear, viscous product showed the $M_w$ to be 115,452 with a polydispersity of 4.48.

EXAMPLE 3

Synthesis of Copoly 4:1(Acrylic:Itaconic) Acid

The reactor of EXAMPLE 1 was charged with 132.9 parts THF. One of the addition funnels was charged with a monomer solution containing 58.6 parts acrylic acid, 26.0 parts itaconic acid and 150.6 parts THF. The other addition funnel was charged with an initiator solution containing 0.82 parts AIBN in 115 parts THF. The reactor vessel was flushed with nitrogen and heated to about 60° C. The monomer solution was added at a rate of about 9 parts every 15 minutes and the initiator solution was added at a rate of about 4.5 parts every 15 minutes. The temperature of the reactor vessel was kept at about 62°-64° C. After the addition of monomer and initiator solutions was complete, the reaction mixture was allowed to stir at approximately about 64° C. for approximately 17 hours, at which time infrared spectral analysis showed that the polymerization reaction was complete.

EXAMPLE 4

Synthesis of Copoly 7:3(Acrylic:Itaconic) Acid

The reactor of EXAMPLE 1 was charged with 134 parts THF and flushed with nitrogen. A monomer solution containing 39 parts itaconic acid, 50.4 parts acrylic acid and 226 parts THF was added at a rate of about 12 parts every 5 minutes. An initiator solution consisting of 0.82 parts AIBN in 51 parts THF was added at a rate of about 2.2 parts every 5 minutes. After addition was complete, the reaction mixture was heated at about 60° C. for approximately 2 hours. Gel permeation chromatography showed the $M_w$ to be 18,310 with a polydispersity of 3.0.

EXAMPLE 5

Synthesis of Copoly 4:1(Acrylic:Maleic) Acid

The reactor of EXAMPLE 1 was charged with 268 parts THF and flushed with nitrogen. A monomer solution containing 23.2 parts maleic acid, 57.6 parts acrylic acid and 88.6 parts THF, was added at a rate of about 6.6 parts every 5 minutes. An initiator solution containing 0.82 parts AIBN in 51.4 parts THF was added at a rate of about 2.2 parts every 5 minutes. The reaction mixture was then allowed to stir for an additional 2 hours at about 60° C. Gel permeation chromatography showed the $M_w$ to be 10,800 with a polydispersity of 2.5.

EXAMPLES 6-8

Reaction of Polyacrylic Acid of EXAMPLE 1 with 2-Isocyanatoethyl Methacrylate Into a three-necked glass reaction vessel fitted with mechanical stirrer, dry air inlet tube, addition funnel and thermometer was transferred a portion of the THF solution of EXAMPLE 1 which contained 24.7 parts polyacrylic acid. To this solution were added sequentially 0.08 parts BHT, 0.08 parts triphenylstibine ("TPS"), 0.135 parts dibutyltin dilaurate ("DBTL"), and an additional 26.6 parts THF. The stirrer was started and the reaction mixture was heated to about 32°-35° C. The amount of 2-isocyanatoethyl methacrylate ("IEM") for each Example was varied as shown in TABLE I. The IEM was added dropwise over a period of approximately 45-50 minutes, so that the reaction temperature did not exceed about 40° C. After the IEM addition was complete, the reaction was stirred at this temperature until the evolution of carbon dioxide ceased. At this point, the heating source was removed and the reaction was allowed to stir at about 20° C. for an additional hour. Infrared spectral analysis showed the absence of the NCO band at 2350 cm$^{-1}$ and the presence of the amide band at 1530 cm$^{-1}$. The homogeneous solution was then transferred to a rotary evaporator and concentrated to a syrupy consistency. The concentrate was added in a thin stream to approximately 500 parts of diethyl ether with agitation, whereupon the polymer precipitated as a fine white solid. The precipitate was filtered, washed with 100 parts of diethyl ether and dried in vacuo. Set out below in TABLE I are the parts of IEM, the yield of polymer, and the viscosity of a 45% solution of the polymer in a mixture of 2-hydroxyethyl methacrylate ("HEMA")/water (2:3 by weight).

TABLE I

| Example | Parts of IEM | Polymer Yield (%) | Viscosity (cstokes) |
| --- | --- | --- | --- |
| 6 | 6.38 | 100 | 233 |
| 7 | 7.97 | 99.9 | 286 |
| 8 | 9.56 | 96.5 | 262 |

EXAMPLE 9

Reaction of Polyacrylic Acid with Allyl Isocyanate

To a solution containing 2.3 parts of the polyacrylic acid prepared as described in EXAMPLE 2 was added 0.005 parts of BHT and 0.01 parts of DBTL. The mixture was stirred to obtain a clear solution. A solution of 0.6 parts of allyl isocyanate in 2 parts of p-dioxane was added dropwise. The reaction mixture was allowed to stir at about 60° C. until the evolution of $CO_2$ ceased. The mixture was then cooled to about 20° C. and allowed to stir for an additional 18 hours. The polymer was precipitated, filtered, washed with hexanes and dried.

EXAMPLE 10

Reaction of Polyacrylic Acid with IEM

2 Parts of DBTL were added, with stirring, to 15 parts of the polyacrylic acid solution of EXAMPLE 2. IEM (7.5 parts) containing 0.05 parts BHT was added dropwise to the mixture. The reaction mixture was stirred at approximately 20° C. for about ½ hour, followed by heating at about 60° C. for approximately 1 hour. Copious evolution of carbon dioxide was observed initially, but ceased as the reaction approached completion. A white material precipitated out initially, but with continued stirring at about 20° C., it gradually dissolved providing a clear solution. The solution was added in a slow stream to diethyl ether; the solid which precipitated was filtered, washed with diethyl ether and dried in vacuo. The dry polymer was dissolved in a 2:3 mixture of HEMA and water.

EXAMPLE 11

Reaction of Copoly(4:1)(Acrylic:Itaconic Acid) with IEM

The polymerized reaction mixture of EXAMPLE 3 was allowed to cool to about 35° C. To the stirred mixture was added 0.15 parts BHT, 0.15 parts TPS and 1.03 parts DBTL. A stream of air was introduced into the reaction mixture, and the reaction temperature was increased to about 40° C. A solution of 35.34 parts IEM dissolved in 22 parts THF was added dropwise over a period of about 1½ hours. The reaction mixture was then allowed to stir at about 40° C. for an additional hour, followed by stirring at about 20° C. for approximately 18 hours. The homogeneous solution was concentrated to a syrupy consistency. It was then precipitated into five times its volume of ethyl acetate. The precipitate was filtered, washed with ethyl acetate and dried in vacuo. The polymer yield was 98%. The dry polymer (45 parts) was dissolved in a mixture containing 33 parts of water and 22 parts of HEMA to yield a homogeneous solution having a viscosity of 276 cstokes.

EXAMPLE 12

Preparation of Light Cure Ionomer Solution

To dried ionomers (prepared from 10 parts of the polyacrylic acid described in EXAMPLE 1, and reacted with 2.08 parts IEM as described in Examples 6–8) were added HEMA and distilled water in the amounts shown in TABLE II. The viscosity of each of the resultant homogeneous solutions was measured.

TABLE II

| Example | Weight % of Ionomer | HEMA | Water | Viscosity (cstokes) |
|---|---|---|---|---|
| 12a | 25 | 28 | 47 | 26 |
| 12b | 25 | 41 | 34 | 35 |
| 12c | 35 | 31 | 34 | 125 |
| 12d | 45 | 21 | 34 | 181 |
| 12e | 45 | 30 | 25 | 185 |

Each of the above ionomer solutions was combined with a polymerization initiator system as follows:

| | |
|---|---|
| Ionomer solution | 4.346 parts |
| Camphorquinone | 0.021 parts |
| Diphenyliodonium chloride | 0.135 parts |

EXAMPLE 13

Measurement of Adhesion to Dentin

Adhesion of light-curable ionomer cement systems to bovine dentin was measured using the following procedure:
1. Apply mixed ionomer cement system to freshly polished (600 grit) bovine dentin.
2. Cure for 20 seconds with dental curing light ("Visilux 2", 3M).
3. Apply dental adhesive ("Scotchbond ™ Dual Cure", 3M).
4. Cure for 20 seconds.
5. Apply light-curable restorative ("P-30", 3M) by molding in the shape of a button.
6. Cure for 20 seconds.
7. Store in water at 37° C. for 24 hours.
8. Shear off button in a tensile ("Instron") at a crosshead speed of 2 mm/min.

A fluoroaluminosilicate glass frit was prepared by fusing together and then cooling the following ingredients.

| Ingredient | Parts |
|---|---|
| $SiO_2$ | 26.84 |
| $Al_2O_3$ | 0.80 |
| $P_2O_5$ | 0.94 |
| $NH_4F$ | 3.32 |
| $AlF_3$ | 20.66 |
| $Na_2AlF_6$ | 10.65 |
| ZnO | 20.66 |
| MgO | 2.12 |
| SrO | 12.55 |

The resulting frit was comminuted to give a fine powder which was then screened through a 44 micron mesh screen. Surface area was determined to be 1.1 $m^2/g$ using a "Monasorb" dynamic flow, single point BET surface area analyzer (Quantachrome Co., Syosset, N.Y.).

Ionomer solutions prepared and combined with a polymerization initiator system as described above in EXAMPLE 12 were mixed with the glass powder at a powder:liquid ratio of 1.4:1 and hand spatulated for approximately 15 seconds at about 20° C. to give a smooth creamy mix. Adhesion results are shown in TABLE III below.

TABLE III

| Ionomer | Adhesion ($kg/cm^2$) |
|---|---|
| 12a | 68.0 |
| 12b | 115 |
| 12c | 125 |
| 12d | 115 |
| 12e | 91 |

In contrast, the adhesion values of commercially available ionomer cement systems, namely "GC Lining Cement", GC Dental Corp., Tokyo, Japan, and "Ketac Bond", Espe Fabrik Pharm. Gmbh, West Germany, were determined by the same method to be 40 $kg/cm^2$ and 45 kg/cm², respectively. The results in TABLE III indicate that the adhesion values of cements prepared from the photocurable ionomer cement systems of the present invention can substantially exceed the adhesion values of the comparable commercially available ionomer cements.

EXAMPLE 14

Effect of Additives in the Reactive Powder

The glass frit prepared as described in EXAMPLE 13 was combined with varying amounts of disodium hydrogen phosphate and milled to form a powder (using 12 mm×12 mm alumina rod media) in a ceramic jar rotated at 60 rpm for about 3 hours. Surface area was determined as described in EXAMPLE 13. The powder was then slurried in a solution containing 1 part diphenyliodonium chloride (polymerization initiator) and 99 parts methanol. The solvent was then evaporated and the dry, initiator-containing powder was screened through a 74 micron mesh screen. Ionomer solutions (prepared as described in EXAMPLE 12d and combined with 0.5% camphorquinone) were mixed with initiator-containing powder at a powder:liquid ratio of 1.4:1 by weight and hand spatulated at approximately 20° C. so as to blend the mixture thoroughly in about 15 seconds using about 30 strokes.

Working time was evaluated by rapidly molding the mixed cement with a spatula into a bead approximately 2.5 cm long and 0.6 cm wide. Forty seconds from the start of the mix a ball applicator was drawn perpendicularly through the bead allowing cement to be pulled across the mixing pad. This procedure was repeated every 10-20 seconds until the cement became excessively stringy or unworkable. Adhesion was determined as described in EXAMPLE 13.

For diametral tensile and compressive strength measurements the mixed cement samples were injected into a glass tube having a 4 mm inner diameter. The filled tube was placed on a vibrator for 30 seconds to eliminate trapped air bubbles, then subjected to 2.88 kg/cm² (40 psi) pressure followed by curing while under pressure, by exposure to a Visilux 2 dental curing light. The cured samples were allowed to stand for 1 hour at about 37° C., 90%+ relative humidity. They were then cut on a diamond saw to form cylindrical plugs 2 mm long for measurement of diametral tensile strength, and 8 mm long for measurement of compressive strength. The plugs were stored in distilled water at approximately 37° C. for about 24 hours and their diametral tensile and compressive strengths were determined according to ISO specification 7489.

The composition of three powders and the concentration of disodium hydrogen phosphate, together with the properties observed for each sample are provided in TABLE IV.

TABLE IV

| | Ex. 14a | Ex. 14b | Ex. 14c |
|---|---|---|---|
| % Na₂HPO₄ | 0 | 1 | 2 |
| Surface area (m²/g) | 1.39 | 1.24 | 1.17 |
| Working time (seconds) | 35 | 135 | 260 |
| Compressive strength (MPa) | — | 93.5 | 68.9 |
| Diametral tensile strength (MPa) | — | 18.1 | 11.6 |
| Adhesion to dentin (kg/cm²) | 89 | 114 | 118 |

The results in TABLE IV indicate that working time can be greatly affected, e.g., prolonged, by the adjustment of the concentration of modifying agent. In this case, the modifying agent is a compound that reacts with the powder in a manner that competes with, and thereby delays the acid-base setting reaction involving the ionomer and powder. The diametral tensile and compressive strengths are somewhat lowered by virtue of such competing reactions, although still remain well within acceptable limits. The adhesion values were not significantly affected.

EXAMPLE 15

Comparison of Various Additives as Modifying Agents

A solution of ionomer prepared as described in EXAMPLE 11 and combined with a polymerization initiator system as described in EXAMPLE 12 was mixed with various additives as shown in TABLES V and VI in an attempt to modify working times of ionomer cement systems of the present invention. The resulting solutions were mixed with a powder obtained by comminuting the glass composition prepared as described in EXAMPLE 13. Working times were determined as described above in EXAMPLE 14. Adhesion was determined as described in EXAMPLE 13.

TABLE V

Effect of Additives on Working Time
Powder surface area 1.04 m²/g
Powder:Liquid ("P/L") ratio 1.4:1

| Additive | Concentration (w/w %) | Working Time (sec) |
|---|---|---|
| None | — | 100-120 |
| Tartaric acid | 1 | 70 |
| Tartaric acid | 3 | 35 |
| Citric acid | 1 | 60-90 |
| Citric acid | 3 | 60-90 |
| Citric acid | 5 | 40 |
| EDTA | 1 | 60-75 |
| Disodium EDTA | 1 | 80 |
| H₃PO₄ | 3 | 100-120 |
| H₃PO₄ | 6 | 60 |
| H₃PO₄ | 12 | 10 |

TABLE VI

Effect of Additives on Working Time and Adhesion
Powder surface area 1.4 m²/g
P/L ratio 1.4:1

| Additive | Concentration w/w % | Working Time (sec) | Adhesion kg/cm² |
|---|---|---|---|
| None | — | 40-60 | 94 |
| Ethanolamine | 3 | 125 | — |
| Triethanolamine | 5 | 200 | — |
| NaH₂PO₄.H₂O | 3 | 390 | 78 |
| NaH₂PO₄.H₂O | 5 | 325 | 86 |
| Na₂HPO₄ | 1 | 120 | 107 |
| Na₂HPO₄ | 3 | 330 | 100 |
| Na₂HPO₄ | 5 | 450 | 65 |
| Na₃PO₄.12H₂O | 7.8 | 400 | — |

Comparison of the data in TABLES V and VI show that acidic additives tend to decrease working time whereas basic additives tend to increase working time.

EXAMPLE 16

Determination of Properties of Set Cements

Polymerization initiator-containing glass powder prepared as described in EXAMPLE 14 was mixed with the ionomer solutions described in EXAMPLES 6-8 (formulated with 0.5% camphorquinone, based on the weight of the liquid), at a powder to liquid weight ratio of 1.4 to 1. The working time and the properties of the set cement after curing by 20 second exposure to a Visilux 2 dental curing light are set forth below in TABLE VII. A commercially available ionomer cement, "GC" brand lining cement, available from GC Dental Corp., was prepared according to its directions as a comparative sample.

TABLE VII

|  | Liquids | | | |
|---|---|---|---|---|
|  | Ex. 6 | Ex. 7 | Ex. 8 | GC |
| Working time (min:sec) | 3:15 | 3:45 | 4:10 | 1:30 |
| Adhesion to dentin (kg/cm$^2$) | 104.5 | 99.5 | 101.2 | 40 |
| Compressive strength (MPa) | 63.7 | 67.5 | 53.2 | 59.0 |
| Diametral tensile strength (MPa) | 11.4 | 12.4 | 11.2 | 5.6 |

The results in TABLE VII indicate that cements of the present invention exhibited equivalent compressive strength and superior adhesion and diametral tensile strength compared to the conventional cement.

EXAMPLE 17

Preparation of Photocurable Ionomers having Ester Linkages

A 15% solution of poly(vinylazalactone) was prepared according to the procedure described in Heilman et al., "Chemistry of Alkenyl Azalactones I. Radiation Sensitive Materials derived from Azlactone Containing Copolymers", *J. Polym. Sci.*, Polym. Chem. Ed. 22, 1179–1186 (1984). The polymer was isolated by precipitating 50 parts of the above solution in 300 parts of mixed hexanes and redissolving the isolated polymer in 24 parts of dry acetone. To this solution were added 1.31 parts of HEMA, 0.02 parts 4-methoxyphenol ("MEHQ") and 0.15 parts of trifluoroacetic acid. The reaction mixture was heated at approximately 60° C. After about 21 hours the azalactone peak at 1820 cm$^{-1}$ decreased due to amide formation, showing that addition of HEMA had occurred. To 18.9 parts of the resulting reaction product were added 0.43 parts of water and 3 parts of trifluoroacetic acid and the resultant mixture was allowed to stir at approximately 20° C. After about 3 days the reaction mixture was considerably more viscous than initially observed. Infrared spectral analysis showed that the azalactone peak had disappeared completely and was replaced by a CO$_2$H peak in the 3000–2500 cm$^{-1}$ region. The polymer was then precipitated in hexanes, filtered and dried in vacuo. A portion (1.09 parts by weight) of the dry polymer was dissolved in 0.80 parts of HEMA and 0.67 parts of polyacrylic acid solution ("Good-rite K-732", B. F. Goodrich, Cleveland, Ohio). To the resulting solution were added 0.091 parts diphenyliodonium chloride and 0.0156 parts camphorquinone. One part of solution was mixed with 1.2 parts of glass powder prepared as described in EXAMPLE 13 and the mixture was irradiated with Visilux dental curing light for 30 seconds. A hard mass was obtained.

EXAMPLE 18

Preparation of Methylvinylether-containing Photocurable Ionomers

20 To a mixture of 1.77 parts of methylvinylether maleic anhydride copolymer ("Gantrez AN119", GAF Corp., New York, N.Y.) in 51 parts of dry tetrahydrofuran was added (1) a solution consisting of 0.34 parts of HEMA, 0.009 parts of MEHQ and 1.6 parts of THF, followed by (2) a solution of 0.015 parts of 1,4 diazabicyclo(2.2.2)octane ("DABCO", Aldrich Chemical Co.) catalyst dissolved in 1.6 parts of THF. The mixture was heated under reflux for about 21½ hours, cooled to approximately 20° C. and then precipitated in hexanes. The pale pink precipitate was filtered, washed with hexanes and dried in vacuo. Infrared and nuclear magnetic resonance spectral analyses indicated that ethylenically unsaturated groups had been linked to the polycarboxylic acid.

EXAMPLE 19

Fluoride Release

In vitro fluoride release was measured for a sample of the cured cement mix of EXAMPLE 13 using the ionomer of EXAMPLE 12c in phosphate buffer of pH 6.4 using a fluoride ion selective electrode according to method of Swartz et al., *J. Dent. Res.*, 63, 158–160 (1984). TABLE VIII below shows the cumulative amount of fluoride leached per gram of the light cured glass ionomer sample, compared with a conventional commercially available glass ionomer cement Ketac Bond (Espe).

TABLE VIII

|  | Fluoride release ($\mu g/g$) | |
|---|---|---|
| Days | Sample | Ketac Bond |
| 1 | 186 | 83 |
| 2 | 176.5 | 161 |
| 3 | 252 | 169 |
| 4 | 370 | 198 |
| 7 | 550 | 298 |
| 11 | 715 | 379 |
| 17 | 900 | 463 |
| 25 | 1110 | 657 |
| 31 | 1235 | 740 |
| 46 | 1665 | 871 |
| 74 | 1791 | 959 |
| 102 | 1950 | 1036 |
| 137 | 2450 | 1140 |
| 203 | 2984 | 1084 |

The light-curable glass ionomer cement system was evaluated in vitro for cariostatic activity using the method developed by R. L. Erickson et al., *J. Dent. Res.*, 66, Abstract No. 1114 (1987). It was found to contain a substantial caries inhibition zone thus indicating that the material should be cariostatic.

I claim:

1. A photocurable ionomer cement system comprising:
   (a) a photocurable ionomer having sufficient pendent ionic groups to undergo a setting reaction in the presence of a reactive powder and water and sufficient pendent polymerizable groups to enable the resulting mixture to be cured by exposure to radiant energy, wherein at least one of said polymerizable groups is linked to said ionomer by means of an amide linkage, and
   (b) reactive powder, the system being suitable for use in the mouth.

2. A photocurable ionomer cement system according to claim 1 further comprising water, present in a form that does not prematurely begin to set the system.

3. A photocurable ionomer cement system according to claim 2 wherein said water is present in the form of an aqueous solution of said ionomer, and said powder is provided as a separate component for mixing with said solution.

4. A photocurable ionomer cement system according to claim 2 wherein said ionomer and said reactive powder are present as an anhydrous mixture and said water is provided as a separate component for mixing with said mixture.

5. A photocurable ionomer cement system according to claim 1 further comprising polymerization initiator.

6. A photocurable ionomer cement system according to claim 1 further comprising cosolvent.

7. A photocurable ionomer cement system according to claim 6 wherein said cosolvent is a copolymerizable cosolvent.

8. A photocurable ionomer cement system according to claim 1 further comprising modifying agent.

9. A photocurable ionomer cement system according to claim 8 wherein said modifying agent is selected from the group consisting of alkanolamines, and mono-, di-, and tri-sodium hydrogenphosphates.

10. A photocurable ionomer cement system comprising
    (a) a photocurable ionomer of the formula $$B(X)_m (Y)_n \quad I$$

wherein;
    B represents an organic backbone,
    each X independently is an ionic group capable of undergoing a setting reaction in the presence of water and a reactive powder,
    each Y independently is a photocurable group, at least one of which Y groups is linked to said backbone by means of an amide linkage,
    m is a number having an average value of 2 or more, and
    (b) reactive powder.

11. A method for preparing a cured ionomer cement comprising the steps of
    (a) mixing a photocurable ionomer having sufficient pendent ionic groups to undergo a setting reaction in the presence of a reactive powder and water and having sufficient pendent polymerizable groups to enable the resulting mixture to be cured by exposure to radiant energy, wherein at least one of said polymerizable groups is linked to said ionomer by means of an amide linkage, (ii) reactive powder, and (iii) water to begin a setting reaction,
    (b) forming the resultant mixture into its desired shape,
    (c) curing the resultant shaped mixture by exposure to radiant energy, and
    (d) allowing said setting reaction to harden said mixture fully.

12. A cured ionomer cement prepared by curing by exposure to radiant energy a photocurable ionomer cement system, said cement system comprising an intimate mixture of
    (a) a photocurable ionomer having sufficient pendent ionic groups to undergo a setting reaction in the presence of a reactive powder and water and having sufficient pendent ethylenically unsaturated groups to enable the resulting mixture to be cured by exposure to radiant energy, wherein at least one of said polymerizable groups is linked to said ionomer by means of an amide linkage,
    (b) reactive powder, and
    (c) water.

13. A photocurable ionomer cement system according to claim 10 wherein said Y group linked by means of an amide linkage is the same as the Y group that is derived from the reaction of a polymer of the formula $B(X)_{m+n}$ with a coupling compound selected from the group consisting of allyl isocyanate, 2-ioscyanatoethyl methacrylate.

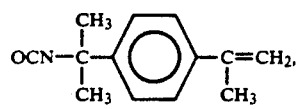

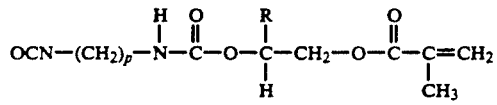

wherein p is 1 to 20 and R is H is lower alkyl (e.g., having 1 to 6 carbon atoms),

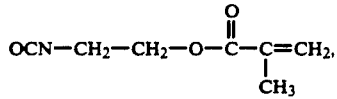

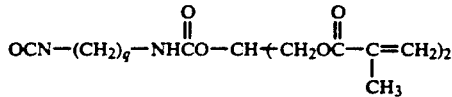

wherein q is 1 to 18,

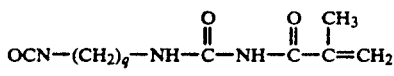

wherein q is as defined above,

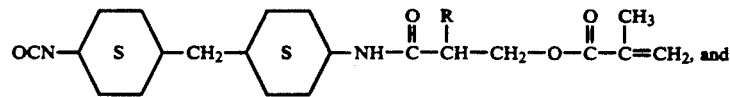

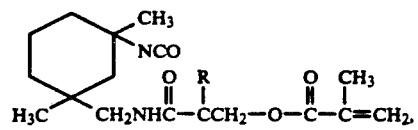

and their corresponding acrylates.

* * * * *

UNITED STATES PATENT AND TRADEMARK OFFICE
CERTIFICATE OF CORRECTION

PATENT NO. : 5,130,347
DATED : July 14, 1992
INVENTOR(S) : Mitra

It is certified that error appears in the above-identified patent and that said Letters Patent is hereby corrected as shown below:

Col. 11, line 7, "tetrahydrofurna" should be --tetrahydrofuran--.

Col. 11, line 17, "minutes" should be --minutes.--.

Col. 11, line 20, "solution" should be --solution.--.

Col. 17, line 60, delete "20".

Col. 19, line 35, "mixing a" should be --mixing (i) a--.

Col. 19, line 32, insert --n is a number having an average value of 1 or more, and--.

UNITED STATES PATENT AND TRADEMARK OFFICE
CERTIFICATE OF CORRECTION

PATENT NO.  : 5,130,347
DATED       : July 14, 1992
INVENTOR(S) : Mitra

It is certified that error appears in the above-indentified patent and that said Letters Patent is hereby corrected as shown below:

Col. 20, line 31, "H is lower" should be --H or lower--.

Signed and Sealed this

Second Day of November, 1993

Attest:

BRUCE LEHMAN

Attesting Officer

Commissioner of Patents and Trademarks